United States Patent [19]

Hodutu

[11] Patent Number: 5,372,815
[45] Date of Patent: Dec. 13, 1994

[54] MEDICINAL COMPOSITIONS FOR USE AS A SKIN MOISTURIZER AND THE TREATMENT OF EXZEMA

[76] Inventor: Mary Hodutu, 3079 Bloor St. West, Etobicoke, Ont., Canada, M8Y 1C7

[21] Appl. No.: 199,795

[22] Filed: Feb. 22, 1994

[51] Int. Cl.$^5$ ................................................. A61K 6/00
[52] U.S. Cl. .................................. 424/401; 424/78.03; 424/195.1
[58] Field of Search ........................ 424/195.1, 401; 514/861

[56] References Cited

U.S. PATENT DOCUMENTS

| | | | |
|---|---|---|---|
| 4,933,177 | 6/1990 | Grollier et al. | 514/861 |
| 5,061,491 | 10/1991 | Deryabin | 424/195.1 |
| 5,104,657 | 4/1992 | Abdulla | 514/861 |
| 5,165,932 | 11/1992 | Horvath | 424/195.1 |
| 5,262,161 | 11/1993 | Dozono | 514/861 |
| 5,292,530 | 3/1994 | McCrea et al. | 514/861 |

*Primary Examiner*—Thurman K. Page
*Assistant Examiner*—Sharon Howard
*Attorney, Agent, or Firm*—Riches McKenzie & Herbert

[57] ABSTRACT

A skin moisturizing medicinal preparation composition comprising Bismuth nitrate, salicylic acid, Catina oil and Rostopasca plant extracts. The composition provides improved moisturizing properties and may be used for a variety of skin conditions. This preparation is particularly useful for treating eczema.

8 Claims, No Drawings

MEDICINAL COMPOSITIONS FOR USE AS A SKIN MOISTURIZER AND THE TREATMENT OF EXZEMA

This invention relates to medicinal formulations for cleansing and moisturizing the skin and more particularly, to a new skin moisturizer which is suitable for the treatment of exzema, comprising Catina oil and Rostopasca powder plant constituents.

BACKGROUND OF THE INVENTION

Many preparations are known in the prior art which contain naturally occurring products having medicinal properties which are formulated to cleanse, moisturize and improve the appearance of the skin. An example of such a preparation comprising Vitamins D and A and protein is disclosed in U.S. Pat. No. 4,223,018. A cosmetic oil including Vitamins A and D and olive oil is disclosed in U.S. Pat No. 2,865,859. A dermatological preparation for topical application to the skin combining protein, acid and vitamins is disclosed in U.S. Pat. No. 2,876,164 and a preparation comprising aloe vera for cleansing and softening the skin is described in U.S. Pat. No. 4,369,180.

SUMMARY OF THE INVENTION

This invention provides novel preparations for moisturizing and cleaning the skin which may also be used for the treatment of exzema.

An object of the invention is thus to provide skin medicinal preparations containing Catina oil obtained from the Romanian plant Hippophoe rhantmoides L, Fam. Elaeognaceae, and Rostopasca obtained from the root of the Romanian plant Chelidonium majus L. Fam. Papaveraceae, to cleanse and moisturize the skin and for the treatment of exzema.

The medicinal preparation according to the invention in its broadest aspect comprises the ingredients and their percentages by weight as follows:

| Ingredient | % w/w |
| --- | --- |
| Bismuth (III) nitrate (5H2O) | 4–10 |
| Salicylic acid (powder) | 4–10 |
| Catina oil | 0.5–5 |
| Rostopasca | 0.3–3 |
| Oil based carrier | 10–90 |

The oil based carrier may be readily selected by the man skilled in the art of skin medicinal preparations from these having acceptable non-irritant and compatible skin properties, while being suitable for providing stable formulations with the active ingredients. Suitable oil based carriers, adjuvants and the like may be selected, for example, from lanolin (hydrous wool), petroleum jellies, particularly VASELINE$^R$ petroleum jelly (Cheesborough-Ponds), and facial moisturizing creams, particularly NIVEA$^R$ Creme (Smith-Nephew).

Preferably, the medicinal compositions according to the invention further comprise olive oil, cod liver oil, vitamin "A" oil and vitamin "F" oil.

The formulations have been found to be most effective when applied as creams to parts of the body, including the face, for moisturizing the skin and for alleviating exzema.

In a preferred aspect the invention provides medicinal preparations comprising the following ingredients:

| Ingredient | % w/w |
| --- | --- |
| Bismuth (III) nitrate (5H2O) | 4–10 |
| Salicylic acid | 4–10 |
| Catina Oil | 0.5–5 |
| Rostopasca | 0.3–3 |
| Vitamin "A" Oil | 0–5 |
| Vitamin "F" Oil | 0–5 |
| Olive Oil | 0–5 |
| Cod Liver Oil | 0–5 |
| Lanolin (hydrous wool) | 0–5 |
| Petroleum Jelly | 10–70 |

In a most preferred embodiment the invention provides a medicinal preparation comprising the following ingredients:

| Ingredient | % w/w |
| --- | --- |
| Bismuth (III) nitrate (5H2O) | about 6.75 |
| Salicylic acid | about 6.75 |
| Catina Oil | about 1.25 |
| Rostopasca | about 0.85 |
| Vitamin "A" Oil | about 0.5 |
| Vitamin "F" Oil | about 0.5 |
| Olive Oil | about 2.5 |
| Cod Liver Oil | about 2.5 |
| Lanolin (hydrous wool) | about 2.5 |
| Vaseline ® Petroleum Jelly | about 42 |
| Nivea ® Creme | about 34 |

Other features, objects and advantages of the present invention are stated in or apparent from the detailed description of the presently preferred embodiment of the invention found hereinbelow.

DETAILED DESCRIPTION OF THE PREFERRED EMBODIMENT

The preparations of the medicinal formulations are accomplished using ingredients commercially available and Catina Oil and Rostopasca extracts prepared from the naturally-occuring plants.

A most preferred organic skin cream medicinal preparation according to the invention is constituted by the composition shown in the Table.

TABLE

| Ingredient | Preparation A % w/w |
| --- | --- |
| Bismuth (III) nitrate (5H2O) | about 6.75 |
| Salicylic acid (powder) | about 6.75 |
| Catina Oil | about 1.25 |
| Rostopasca | about 0.85 |
| Vitamin "A" Oil | about 0.5 |
| Vitamin "F" Oil | about 0.5 |
| Olive Oil | about 2.5 |
| Cod Liver Oil | about 2.5 |
| Lanolin (hydrous wool) | about 2.5 |
| Vaseline ® Petroleum Jelly | about 42 |
| Nivea ® Creme | about 34 |

Romanian Rostopasca roots (Chelidonium majus, L. Fam. Papaveraceae) are ground and soaked in an aqueous cod liver oil mixture for 16–20 days in the earth.

The preferred Catina Oil constituent of use in the present invention is the orange-yellow oil extracted from the fruit of the rusty yellow leafed Hippophoe plant Hippophoe rhammoides, L,, Fam, Elaeognaceae) obtained from the Carpathean Mountains of Eastern Europe.

The preferred lanolin of use in the practice of the invention is extracted from the organic solvent used in the washing of hydrous wool and is constituted as a light yellow wax.

Vaseline[R] petroleum jelly is a commercial product of a mixed long-chain paraffin wax obtained from the purification and whitening of the residue of the distillation of petroleum.

Bismuth nitrate, salicylic acid, olive oil and Vitamins A (retinol) and F were obtained from commercial sources.

The preparation of Preparation A shown in the TABLE is accomplished in the following manner.

A first mixture of bismuth nitrate, salicylic acid and Vitamins A and F in olive oil is prepared by admixture and grinding of their ingredients.

A second mixture consisting of the Rostopasca mixture and Catina oil obtained as hereinabove described is mixed with melted pure lanolin and Vaseline[R] petroleum jelly over a steam bath to provide a homogenized mixture, which is subsequently mixed with NIVEA[R] creme to provide a further homogenized mixture.

The first and second mixtures are, individually, gently heated on a steam bath, then mixed and stirred together to provide the medicinal cream product.

The preparations according to the invention are preferably provided in the form of a cream formulation. Although the preferred preparations are formulated as described hereinabove it should be understood that various modifications thereto can be prepared, which modifications could require the skill of the man in the formulation art to provide stable and effective emulsion formulations. However, it should be recognized that in the preparation of the preferred embodiment described hereinabove, that extreme variations in the ratios of ingredients as set forth in the Table may result in the production of unsatisfactory and unstable viscous mixtures.

Preferably, Preparation A is used as an overnight skin cream for the treatment of exzema by the application thereof to the skin of the face and body.

Although this disclosure has described and illustrated certain preferred embodiments of the invention, it is to be understood that the invention is not restricted to these particular embodiments, but, rather, the invention includes all embodiments which are functional or chemical equivalents of the specific embodiments and features that have been described.

I claim:

1. A skin moisturizing medicinal composition comprising the following ingredients in the following percentages by weight in the final composition:

| Ingredient | % w/w |
| --- | --- |
| Bismuth (III) nitrate (5H$_2$O) | 4–10 |
| Salicylic acid (powder) | 4–10 |
| Catina oil | 0.5–5 |
| Rostopasca | 0.3–3 |
| lanolin or petroleum jelly | 10–90. |

2. A composition as claimed in claim 1 further comprising a natural oil selected from Vitamin A oil, Vitamin F oil, olive oil and cod liver oil.

3. A skin moisturizing medicinal composition comprising the following ingredients expressed as a percent by weight:

| Ingredient | % w/w |
| --- | --- |
| Bismuth (III) nitrate (5H$_2$O) | 4–10 |
| Salicylic acid | 4–10 |
| Catina Oil | 0.5–5 |
| Rostopasca | 0.3–3 |
| Vitamin "A" Oil | 0–5 |
| Vitamin "F" Oil | 0–5 |
| Olive Oil | 0–5 |
| Cod Liver Oil | 0–5 |
| Lanolin (hydrous wool) | 0–5 |
| Petroleum Jelly | 10–70. |

4. A skin moisturizing medicinal composition comprising the following ingredients expressed as a percent by weight:

| Ingredient | % w/w |
| --- | --- |
| Bismuth (III) nitrate (5H$_2$O) | about 6.75 |
| Salicylic acid | about 6.75 |
| Catina Oil | about 1.25 |
| Rostopasca | about 0.85 |
| Vitamin "A" Oil | about 0.5 |
| Vitamin "F" Oil | about 0.5 |
| Olive Oil | about 2.5 |
| Cod Liver Oil | about 2.5 |
| Lanolin (hydrous wool) | about 2.5 |
| Petroleum Jelly | about 42 |
| Facial Moisturizing Cream". | about 34 |

5. A medicinal composition as claimed in claim 1 for the treatment of exzema comprising the following ingredients in the following percentages by weight in the final composition:

| Ingredient | % w/w |
| --- | --- |
| Bismuth (III) nitrate (5H$_2$O) | 4–10 |
| Salicylic acid (powder) | 4–10 |
| Catina oil | 0.5–5 |
| Rostopasca | 0.3–3 |
| lanolin or petroleum jelly | 10–90. |

6. A composition as claimed in claim 5 further comprising a natural oil selected from Vitamin A oil, Vitamin F oil, olive oil and cod liver oil.

7. A medicinal composition as claimed in claim 1 for the treatment of exzema comprising the following ingredients expressed as a percent by weight:

| Ingredient | % w/w |
| --- | --- |
| Bismuth (III) nitrate (5H$_2$O) | 4–10 |
| Salicylic acid | 4–10 |
| Catina Oil | 0.5–5 |
| Rostopasca | 0.3–3 |
| Vitamin "A" Oil | 0–5 |
| Vitamin "F" Oil | 0–5 |
| Olive Oil | 0–5 |
| Cod Liver Oil | 0–5 |
| Lanolin (hydrous wool) | 0–5 |
| Petroleum Jelly | 10–70. |

8. A medicinal composition as claimed in claim 1 for the treatment of exzema comprising the following ingredients expressed as a percent by weight:

| Ingredient | % w/w |
| --- | --- |
| Bismuth (III) nitrate (5H$_2$O) | about 6.75 |
| Salicylic acid | about 6.75 |
| Catina Oil | about 1.25 |
| Rostopasca | about 0.85 |
| Vitamin "A" Oil | about 0.5 |
| Vitamin "F" Oil | about 0.5 |
| Olive Oil | about 2.5 |
| Cod Liver Oil | about 2.5 |
| Lanolin (hydrous wool) | about 2.5 |
| Petroleum Jelly | about 42 |
| Facial Moisturizing Cream". | about 34 |

* * * * *